(12) United States Patent
Dhurjaty

(10) Patent No.: US 6,597,949 B1
(45) Date of Patent: Jul. 22, 2003

(54) MECHANICALLY POWERED EXTERNAL DEFIBRILLATOR

(76) Inventor: Sreeram Dhurjaty, 115 Sylvania Rd., Rochester, NY (US) 14618-3705

( * ) Notice: Subject to any disclaimer, the term of this patent is extended or adjusted under 35 U.S.C. 154(b) by 214 days.

(21) Appl. No.: 09/696,379

(22) Filed: Oct. 25, 2000

(51) Int. Cl.⁷ .................................................. A61N 1/40
(52) U.S. Cl. .................................. 607/5; 607/8; 607/15
(58) Field of Search ............................... 607/5, 6, 7, 8, 607/15, 9, 40, 124, 142

(56) References Cited

U.S. PATENT DOCUMENTS 5,385,575 A * 1/1995 Adams ........................... 607/5
5,431,687 A * 7/1995 Kroll .............................. 607/8
6,353,758 B1 * 3/2002 Gliner et al. ................... 607/5

* cited by examiner

*Primary Examiner*—Tu Ba Hoang
(74) *Attorney, Agent, or Firm*—Greenwald & Basch LLP; Howard J. Greenwald

(57) ABSTRACT

A defibrillator which contains a device for producing alternating voltage, a power factor controller for converting the alternating voltage to a direct voltage, and a device for converting the direct voltage into a biphasic waveform voltage. The defibrillator also contains a device for sensing the electrical activity of a human heart and for allowing one to hear an audio signal corresponding to such activity.

20 Claims, 11 Drawing Sheets

MECHANICALLY POWERED EXTERNAL DEFIBRILLATOR

FIELD OF THE INVENTION

A defibrillator powered by mechanical means which allows an operator to listen to an analog signal corresponding to a patient's electrocardiogram activity.

BACKGROUND OF THE INVENTION

Defibrillators are well known to those skilled in the art; see, e.g., U.S. Pat. No. 6,041,254 of Joseph Sullivan et al., the entire disclosure of which is hereby incorporated by reference into this specification.

A defibrillator is a device which treats an abnormal heart condition called fibrillation, in which the heat beats randomly; fibrillation will often cause death if not reversed within a few minutes of its occurrence. Defibrillators are devices which attempt to reverse fibrillation.

Defibrillators are generally powered either by mains and/or by batteries. This poses no substantial problem in the developed countries, such as the United States. In developing countries, however, there often is not ready access to either main power or battery power.

Even when batteries are available to power defibrillators, they invariably lose their power over time; and there is a risk that, in a life-threatening situation, a battery-powered defibrillator may not function. Consequently, the manufacturers of battery-powered defibrillators suggest that the batteries therein be checked frequently, a suggestion which is as often ignored as is followed.

Furthermore, many of the battery-powered defibrillators contain lithium batteries, which, in at least one recently reported occurrence, exploded.

It is an object of this invention to provide a defibrillator which can be operated by mechanical means and need not rely upon either mains or battery power.

It is another object of this invention to provide a defibrillator which will allow an operator to monitor a patient's electrocardiogram and to determine when the defibrillation is necessary.

SUMMARY OF THE INVENTION

In accordance with this invention, there is provided a defibrillator which is mechanically powered and in which a direct voltage is generated and applied to a patient's heart to stop fibrillation. The defibrillator also contains a device which senses the electrical pulses generated by the patient's heart and converts these sensed pulses into an audio output which can be monitored by the person using the machine.

BRIEF DESCRIPTION OF THE DRAWINGS

The invention will be described by reference to the specification and to the drawings, in which like numbers refer to like elements, and in which.

DESCRIPTION OF THE PREFERRED EMBODIMENTS

Figure 1:
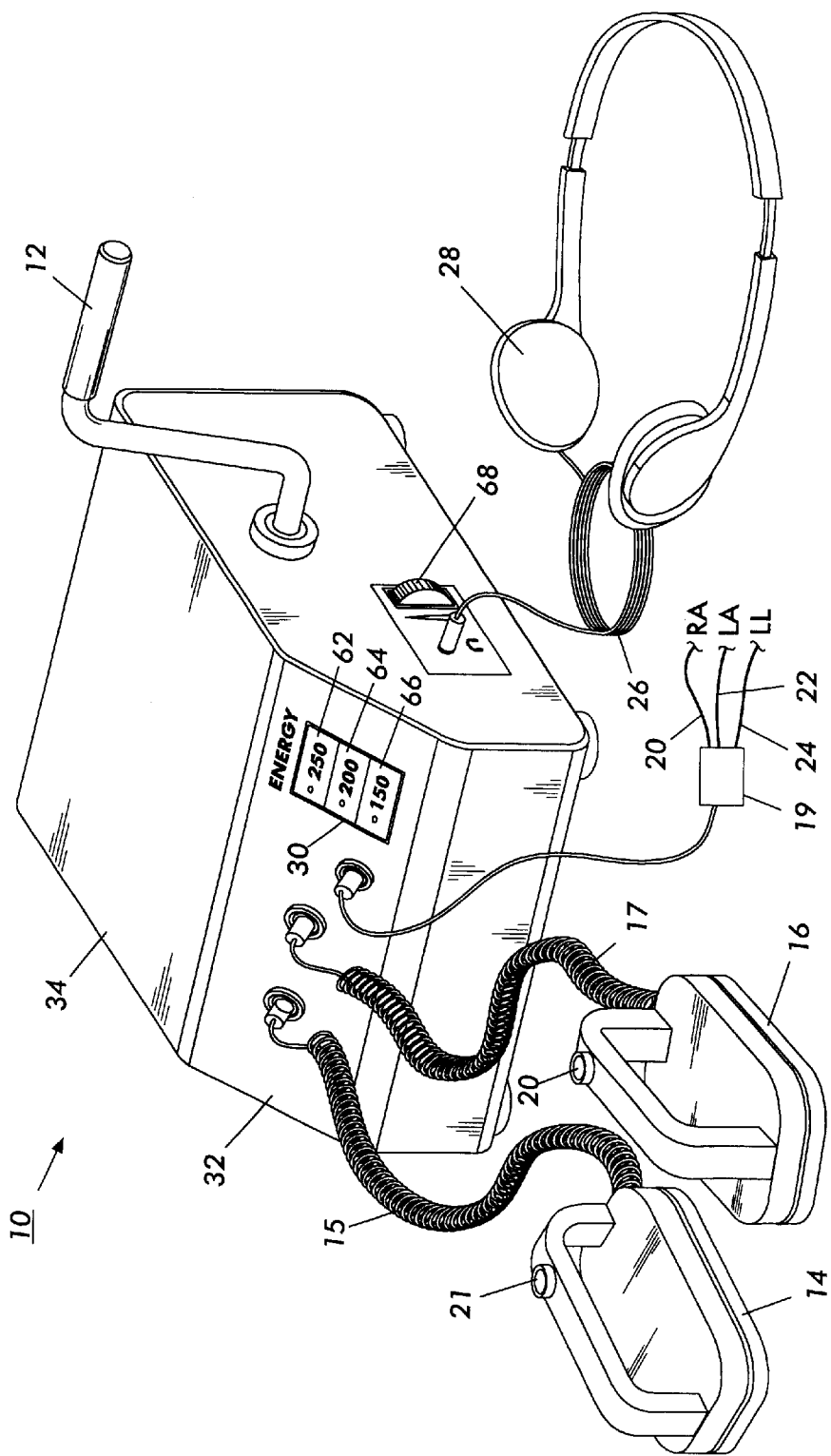
FIG. 1 is a perspective view of one preferred defibrillator of the invention.

FIG. 1 is a perspective view of a defibrillator 10 which, in the preferred embodiment depicted, is comprised of a hand crank 12 connected to a mechanical means for producing alternating voltage (not shown in FIG. 1), a defibrillator paddle 14, a defibrillator paddle 16, a cable 18 with extensions 20 (for the patient's right arm), 22 (for the patient's left arm), and 24 (for the patient's left leg), a cable 26 which is adapted to provide an audio output to headphones 28, and a switch/display assembly 30 disposed on the front 32 of casing 34. Switches 21 and 23 allow the discharge of energy into the patient by the operator.

As is known to those skilled in the art, the defibrillator paddles 14 and 16 are connected anteriorly and laterally on the patient's chest. These paddles, and their use, are well known and are described, e.g., in U.S. Pat. Nos. 6,174,468, 6,128,530, 6,097,987, 6,097,982, 6,075,369, 6,064,906, 6,041,254, 5,999,852.

It is preferred that paddles 14 and 16 consist essentially of stainless steel to effectively conduct the high voltage passed through high voltage cables 15 and 17.

The high voltage delivered to paddles 15 and 17 preferably is a biphasic waveform. As is known to those skilled in the art, a biphasic waveform is a waveform with two successive pulses of opposite polarities. These waveforms are well known in the defibrillation art; see, e.g., U.S. Pat. Nos. 6,119,039, 6,112,118, 6,104,954, 6,104,953, 6,101,413, 6,085,116, 6,041,255, 5,891,172.

Biphasic waveforms are also described in articles by Geddes et al. ("Evolution of optimum bidirectional wave for defibrillation, "Biomedical Instrumentation Technology 2000, January-February; 34,(1):39–54), by Yamanouchi et al. ("Fully discharging phases. A new approach to biphasic waveforms for external defibrillation," Circulation 1999 August 24:100(8):826–31), by Greene ("Comparison of monophasic and biphasic defibrillating pulse waveforms . . . ", American Journal of Cardiology Jun. 1; 1995 75(16):1135–9).

Figure 1A:
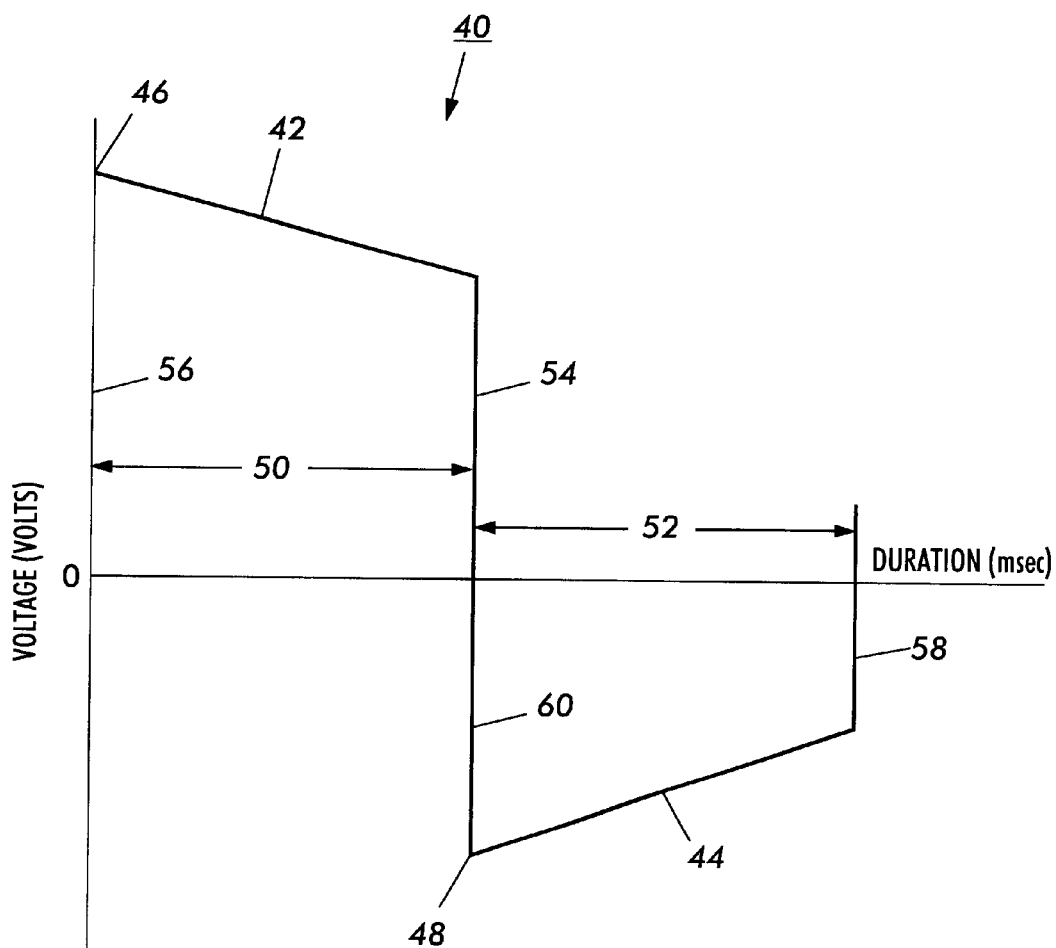
FIG. 1A is a graph of a biphasic voltage produced by the defibrillator of FIG. 1.

FIG. 1A is graph of voltage versus time, illustrating one preferred biphasic waveform produced by defibrillator 10. Referring to FIG. 1A, it will be seen that biphasic waveform is comprised of a positive pulse 42 and a negative pulse 44. The peak voltage 46 of pulse 42 generally exceeds the peak voltage 46 of pulse 48, generally being at least 2 times as great. In the preferred embodiment depicted in FIG. 2A, peak voltage 46 is plus 1800 volts, and peak voltage 48 is minus 600 volts.

It will be appreciated that, although one preferred biphasic waveform is illustrated in FIG. 1A, other such waveforms with a trapezoidal shape also may be used.

In the preferred embodiment depicted in FIG. 1A, the duration 50 of pulse 42 is preferably from about 3 to about 12 milliseconds. The duration 52 of pulse 44 also is from about 3 to about 12 milliseconds.

In such preferred embodiment, it is preferred that each of pulses 42 and 44 be a trapezoidal or "exponentially truncated" wave with a tilt of from 40 to about 70 percent. The tilt of pulse 42 is the ratio of voltage 54 to voltage 56, and the tilt of pulse 44 is the ratio of voltage 58 to voltage 60.

Referring again to FIG. 1, it will be seen that a separate cable 18 is employed to sense the electrical manifestations of the patient's heart activity. The cable is connected to electrodes 20, 22, and 24 via connector 19 which are connected, respectively, to the patient's right arm, left arm, and left leg.

These electrocardiogram cables are well known to those skilled in the art and are described, e.g., in U.S. Pat. Nos. 6,134,468, 6,117,076, 6,115,623, 6,097,987, 6,075,369.

Referring again to FIG. 1, and in the preferred embodiment depicted therein, it will be seen that switch/display assembly 30 is comprised switches and indicators. By pressing either switch 62 or 64 or 66, one may choose an energy output of either 250 Joules, or 200 Joules, or 150 Joules. It is preferred that a light emitting diode (not shown) illuminate the value of energy chosen.

In the preferred embodiment illustrated in FIG. 1, volume control 68 controls the volume of the audio signal delivered to cable 26 and headphones 28.

The means for delivering the audio signal depicted in FIG. I is a set of headphones 28. As will be apparent to those skilled in the art, other suitable means may be used such as, e.g., earphones, speakers, etc.

The casing 34 preferably is a durable enclosure which may be made from plastic material, steel, aluminum, etc.

Figure 2:
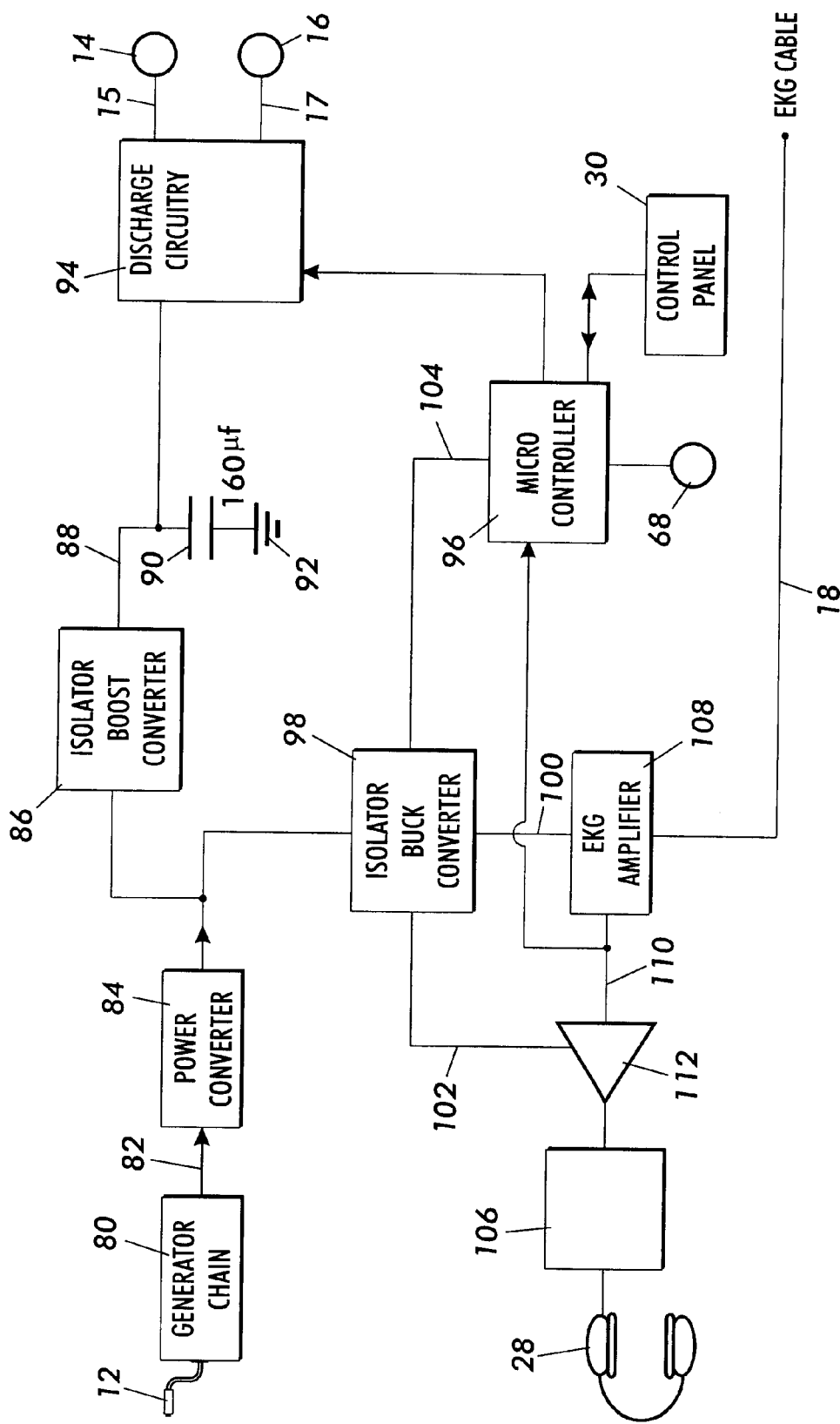
FIG. 2 is a block diagram of the defibrillator of FIG. 1.

FIG. 2 is a block diagram illustrating the defibrillator 10 of FIG. 1. Referring to FIG. 2, and in step 80, crank 12 is used to power a multiplicity of generators, such bicycle dynamos. One may use only one such bicycle dynamo, although it is preferred to use at least two such dynamos. In one preferred embodiment, at least three such dynamos are used. In another embodiment, at least four such dynamos used. It is preferred to use from 4 to 8 such dynamos.

Although FIGS. 1 and 2 have illustrated one preferred mechanical means for generating electrical energy, it will be apparent that other such means also may be used. Thus, e.g., one may wind up a spring which, as it uncoils, drives one or more generators. Thus, one may use pedal power to power one or more generators. Thus, one may use an air turbine powered by a compressor, which is manually operated and/or is run off of compressed air. Other suitable mechanical means will be readily apparent to those skilled in the art.

The preferred bicycle dynamos are commercially available. Thus, by way of illustration and not limitation, they may be purchased from the Miller Industries Company of India as a 12 volt, six watt dynamo. Thus, by way of illustration and not limitation, one may use one or more of the bicycle dynamos disclosed in U.S. Pat. Nos. 6,118,196, 6,109,770, 6,104,096, 6,037,690, 6,016,022, 5,932,943, 5,895,991, 5,874,792.

The bicycle dynamo described in U.S. Pat. No. 6,118,196 is illustrative of those which may be used. This bicycle dynamo contains a large number of magnets in alternate polarity lined up at a fixed interval along the inner circumference of a rotating mechanism. A circular lining is outfitted and anchored along the perimeter of the main axle with a transformer strapped to it.

Referring again to FIG. 2, the generator chain used in step 80 producing an alternating voltage with a frequency dependent upon how fast crank 12 is rotated. Generally, the frequency will be from 50 to about 600 cycles per second.

Depending upon the number of dynamos used, the output from the generator chain will preferably be from about 12 to about 36 watts, generally corresponding to an alternating voltage of from about 24 to about 72 volts.

The output from the generator chain is passed via line 82 to power converter 84. The power converter converts the A.C. voltage from the generator chain to direct voltage at an efficiency of at least about 70 percent and, more preferably, at least about 90 percent.

In one preferred embodiment, the power converter used in step 84 is a power factor controller with an input power factor of at least about 0.80 and, more preferably, at least about 0.95. The power factor controllers are well known and are described, e.g., in U.S. Pat. Nos. 4,074,344, 4,677,366, 4,777,409, 4,801,887, 4,816,982, 4,831,508, 4,940,929, 5,003,454, 5,181,159, 5,528,126 5,301,095.

Power factor controllers with an input power factor of at least about 0.99 are readily commercially available. They may be purchased, e.g., as part number UC 3853 from the Unitrode Integrated Circuits Corporation of Merrimack, N.H.

As is known to those skilled in the art, power factor controllers preferably convert an alternating current waveform with a specified voltage to a to a direct voltage with a higher direct voltage at an efficiency of at least about 85 percent.

Referring again to FIG. 2, the direct current produced in step 84 is preferably divided so that it can function in two separate circuits.

In step 86, a portion of the direct voltage is fed to an isolated boost converter which steps up the voltage of the direct voltage input. Typically, about 200 volts will be fed into isolated boost converter 86, and the output from such converter 86 will often be about 1800 volts. These isolated boost converters are well known to those skilled in the art and are described, e.g., in U.S. Pat. Nos. 6,128,205, 6,104, 172, 6,101,108, 6,088,250, 6,069,801.

Referring again to FIG. 2, the boosted direct current is fed via line 88 to a stack of capacitors 90 which preferably contains from about 8 to about 12 capacitors in parallel and/or in parallel. The total capacitance of the capacitor arrangement is preferably at least about 120 microfarads and, more preferably, is at least about 160 microfarads. The stack of capacitors 90 is preferably connected to a ground 92.

As will be apparent to those skilled in the art, the capacitors 90 store electrical energy which can be discharged into the patient (not shown) upon demand. It preferably takes from about 20 to about 40 seconds to charge the capacitors 90; and the charged capacitors 90 will typically discharge in a period of from about 6 to about 24 milliseconds. The power of the discharge pulses is substantially greater than the power of the energy being fed to the capacitors.

Referring again to FIG. 2, a discharge circuit 94 controlled by microcontroller 96 governs the rate of discharge of capacitors 90 in order to produce the desired biphasic waveform, which is discussed elsewhere in this specification. The desired biphasic waveform is delivered via cables 15 and 17 to paddles 14 and 16, respectively.

The other circuit fed by the direct current from power converter 84 is comprised of an isolated buck converter which reduces the direct voltage. Typically, e.g., the direct voltage is reduced from about 200 volts to less than ten volts. Thus, e.g., 8 volts can be delivered via lines 100 and 102, and 5 volts can be delivered via line 104. Similarly, 8 volts can similarly be delivered to modulator 106.

Buck converters are well known to those skilled in the art and are described, e.g., U.S. Pat. Nos. 6,087,815, 6,067,241, 6,008,999, 5,999,419.

The microcontrollers control the discharge circuitry 94. It, in turn, is controlled by the control panel 30 and the volume control 68. The microcontroller also processes an electrocardiogram signal from EKG amplifier to monitor such signal and to insure that the output to paddles 14 and 16 is appropriate in intensity, waveform, and timing. The EKG amplifier is fed information by EKG cable 18 which transmits signals via connector 19 from electrodes 20, 22, and 24 on the patient.

Signals from the EKG amplifier 108 are also fed via line 110 to audio amplifier, which provides a filtered and amplified signal to modulator 106. Modulator 106 preferably provides a frequency and/or an amplitude modulated output 106 which can be monitored in headphones 28.

Figure 3:
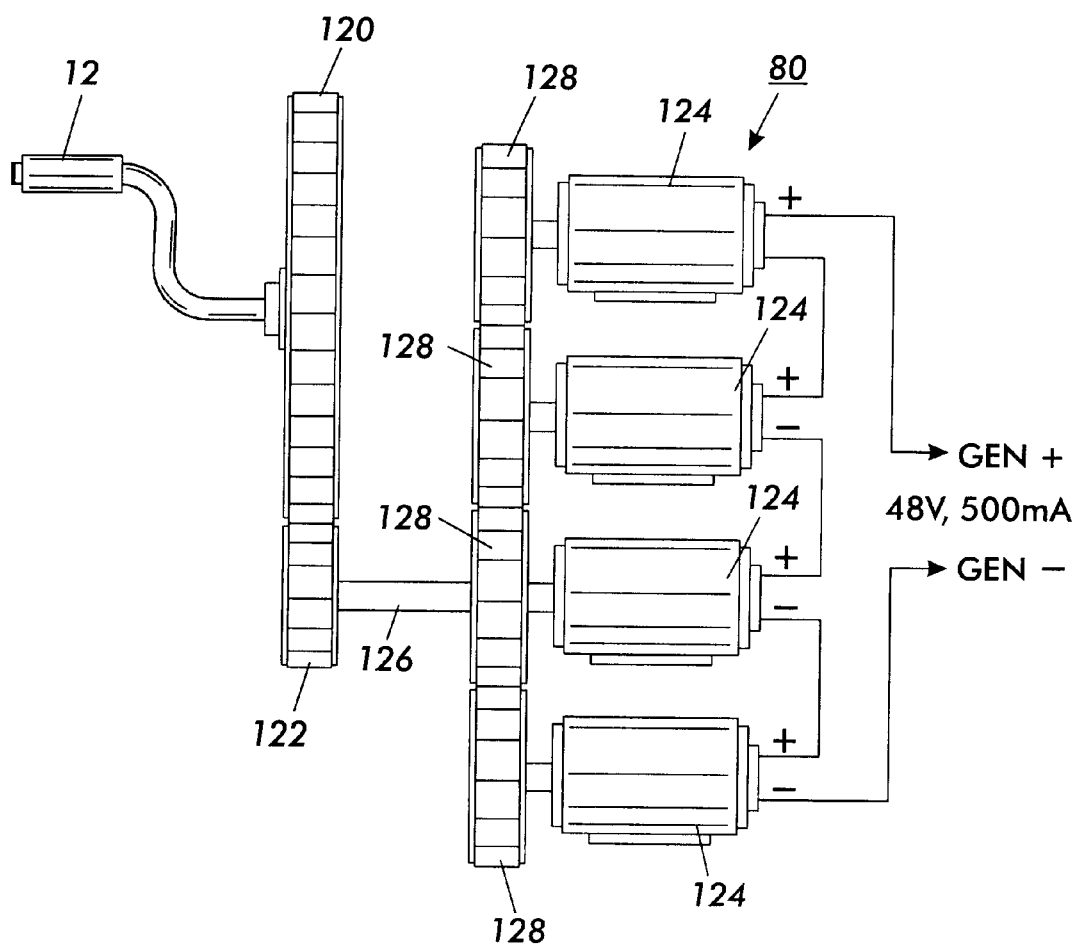
FIG. 3 is a schematic of one preferred mechanical means for producing direct voltage for the defibrillator of FIG. 1.

FIG. 3 is a schematic representation of a generator chain 80 operatively connected to the crank 28. In the embodiment depicted, the crank 28 is connected to a gear 120 which engages gear 122. Because gear 120 has substantially more gear teeth than gear 122, one revolution of gear 120 produces several revolutions of gear 122. It is preferred to use gearing such that one turn of gear 120 will produce at least 80 turns of for each of the dynamos 124. Means for producing such a gear ratio are well known. In the embodiment depicted in FIG. 3, gear 122 is connected via shaft 126 to a multiplicity of gears 128, each of which is connected to one of dynamos 124.

In one embodiment, each of dynamos 124 produces a 500 milliampere 12 volt alternating current.

As will be apparent, fewer or more dynamos 124 may be used, and different gearing arrangements also may be used.

Figure 4A:
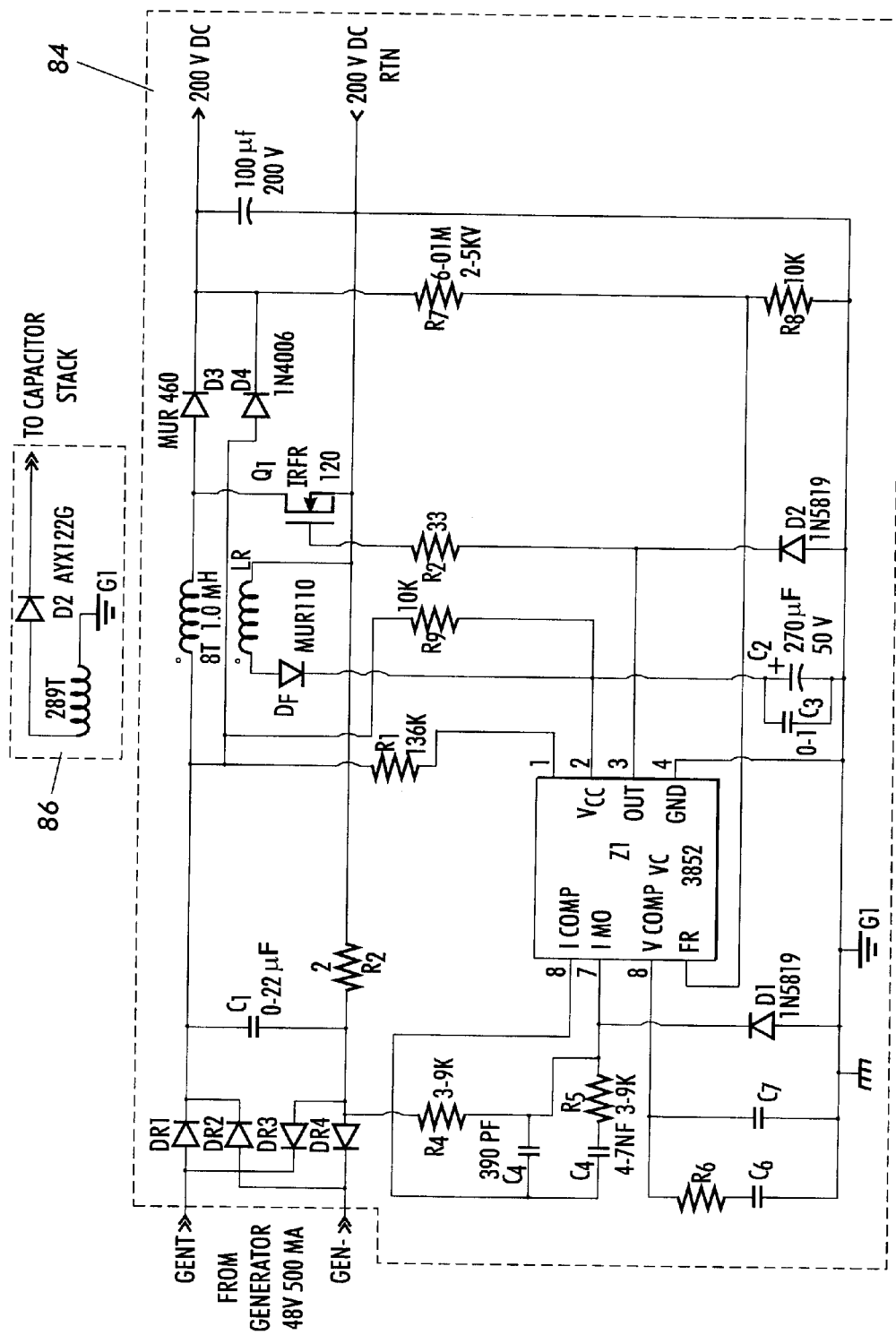
FIGS. 4A and 4B are schematics illustrating different means of converting power produced by mechanical means into desired defibrillation outputs.
Figure 4B:
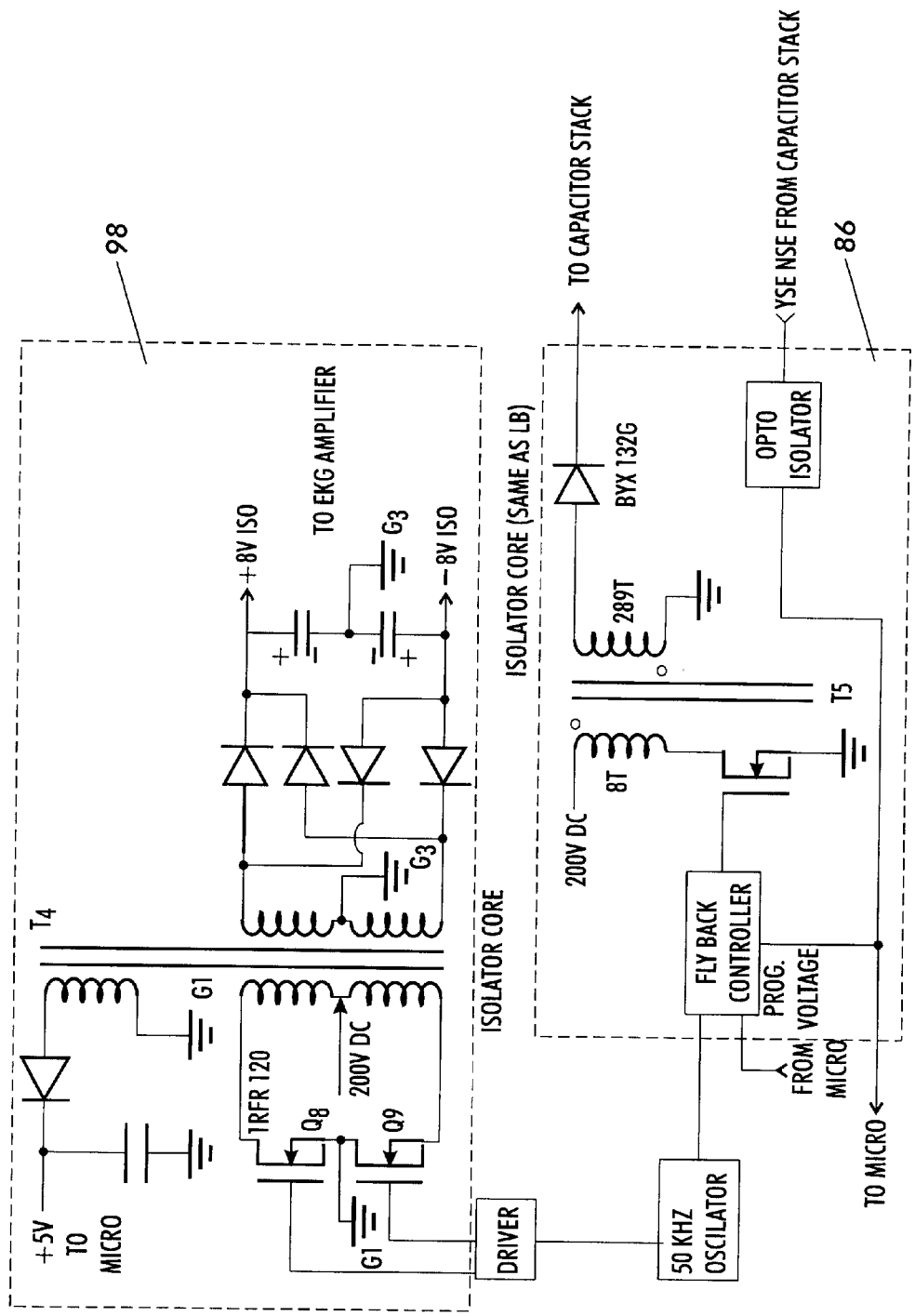

FIG. 4A is a schematic of one preferred power converter 84 and one preferred isolated boost converter 86. FIG. 4B is a schematic of another preferred isolated boost converter 86 and a preferred isolated buck converter 98.

Figure 5:
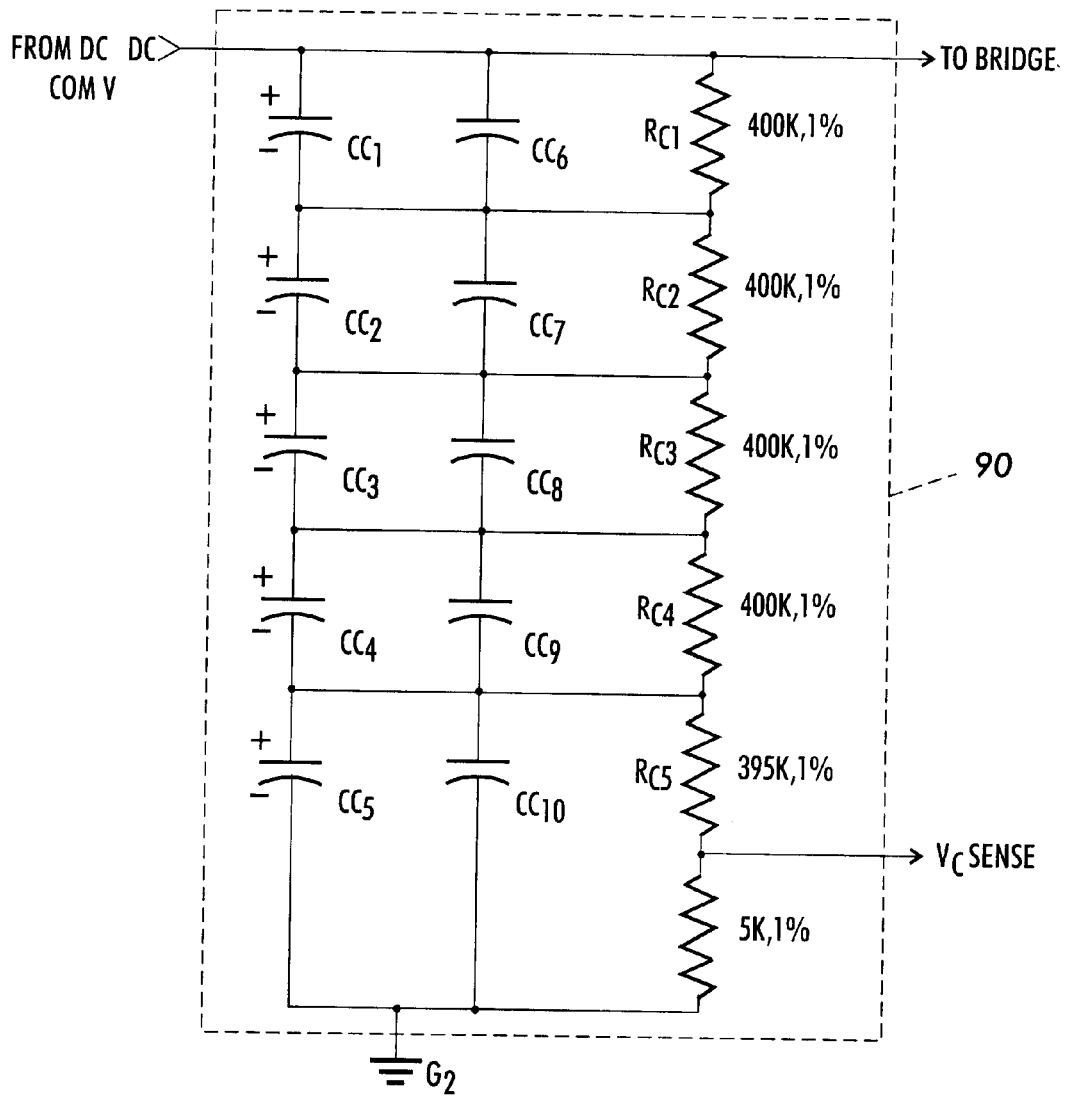
FIG. 5 is a schematic illustrating one means of storing electrical energy produced by mechanical means.

FIG. 5 is a schematic of one preferred charging stack 90. In the embodiment depicted in FIG. 5, capacitors CC1 through CC10 are preferably photoflash capacitors with a capacitance of 400 micofarads and a capacity of 400 volts matched to 5 percent. These photoflash capacitors are well known and may be purchased, e.g., from the Rubycon Company of Japan. Reference also may be had, e.g., to U.S. Pat. Nos. 6,111,264, 5,439,482, 4,676,617, 4,464,608, 4,225,691.

Figure 6A:
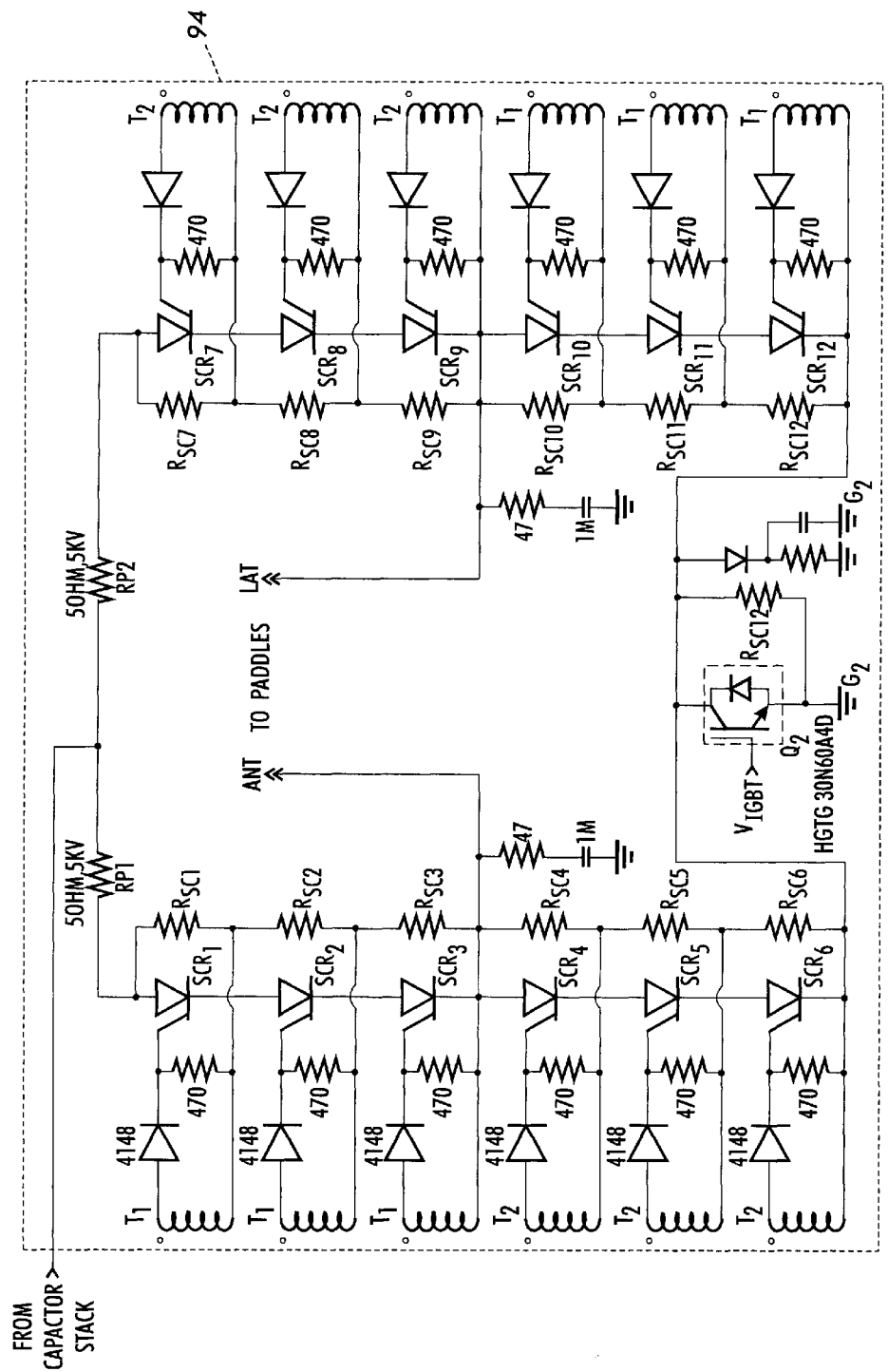
FIGS. 6A, 6B, and 6C are schematics of preferred discharged circuits.
Figure 6B:
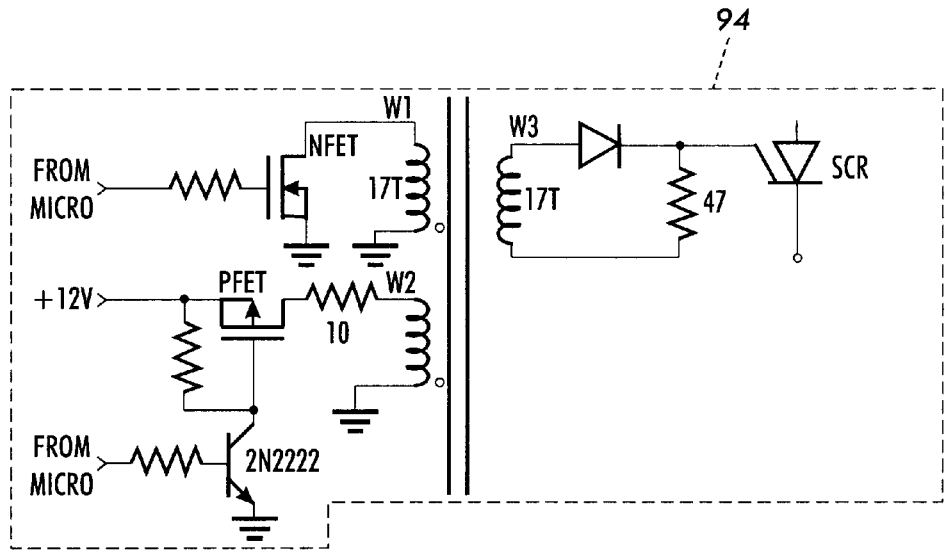
Figure 6C:
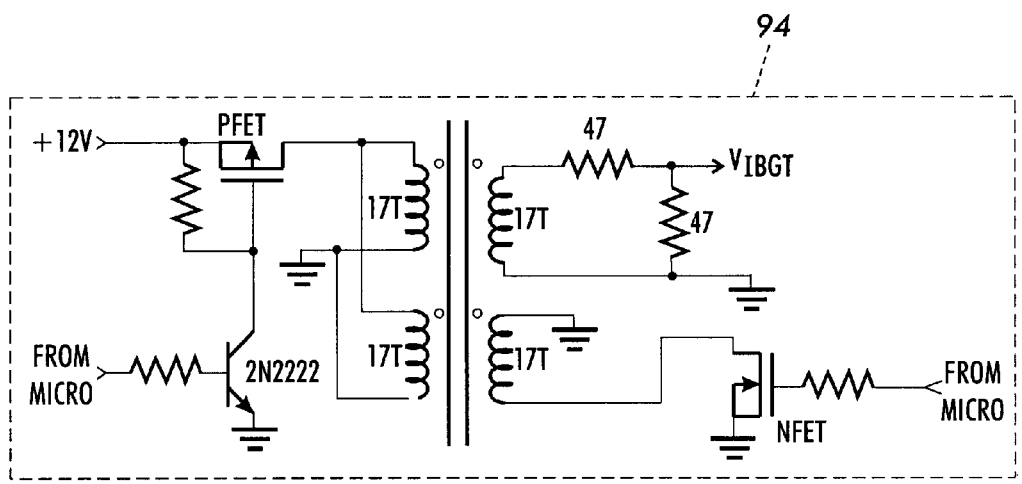

Each of FIGS. 6A, 6B, and 6C is a schematic of a preferred embodiment of a discharge circuit 94. With regard to these FIG.s, it should be noted that: (1) all silicon controlled rectifiers are preferably Motorola MRC265-10, (2) each of resistors RSC1 through RSC13 has a tolerance of 1 percent and a resistance of about 2.82 megohms, the insulated gate bipolar transistor Q2 used is Intersil HGTG 30N60A4D, (3) for the sake of simplicity of representation in FIG. 6B, only one of the six transformer windings used is shown, (4) the circuit of FIG. 6A is an "H bridge" for generating a biphasic waveform, (5) the circuits of FIGS. 6B and 6B are control circuits.

Figure 7:
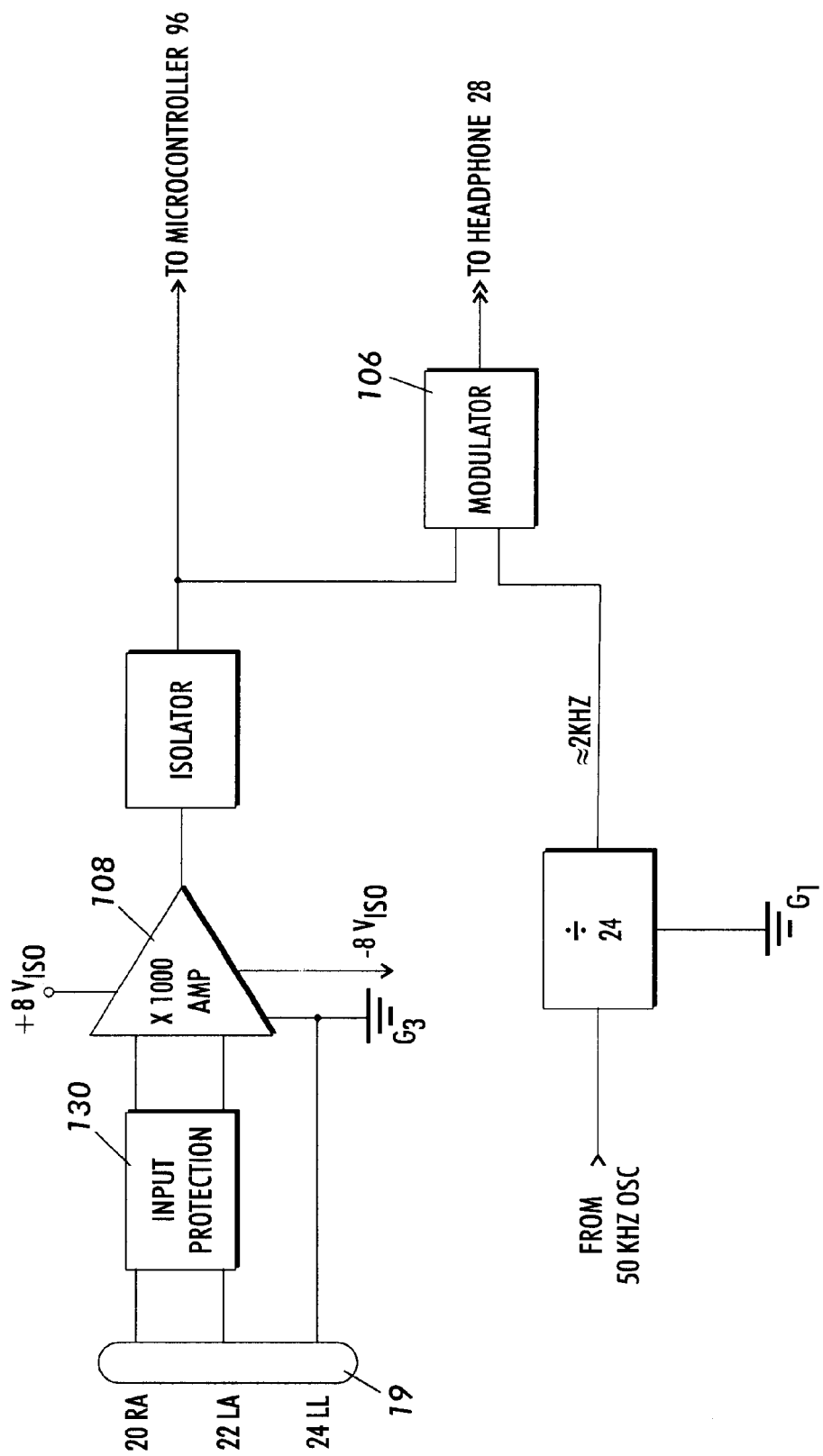
FIG. 7 is a schematic of a preferred electrocardiogram amplifier circuit with input protection.

FIG. 7 is a schematic of an EKG amplifier 108 with an input protection circuit 130 which, in turn, is connected to an EKG connector 19 (see FIG. 1).

Figure 8:
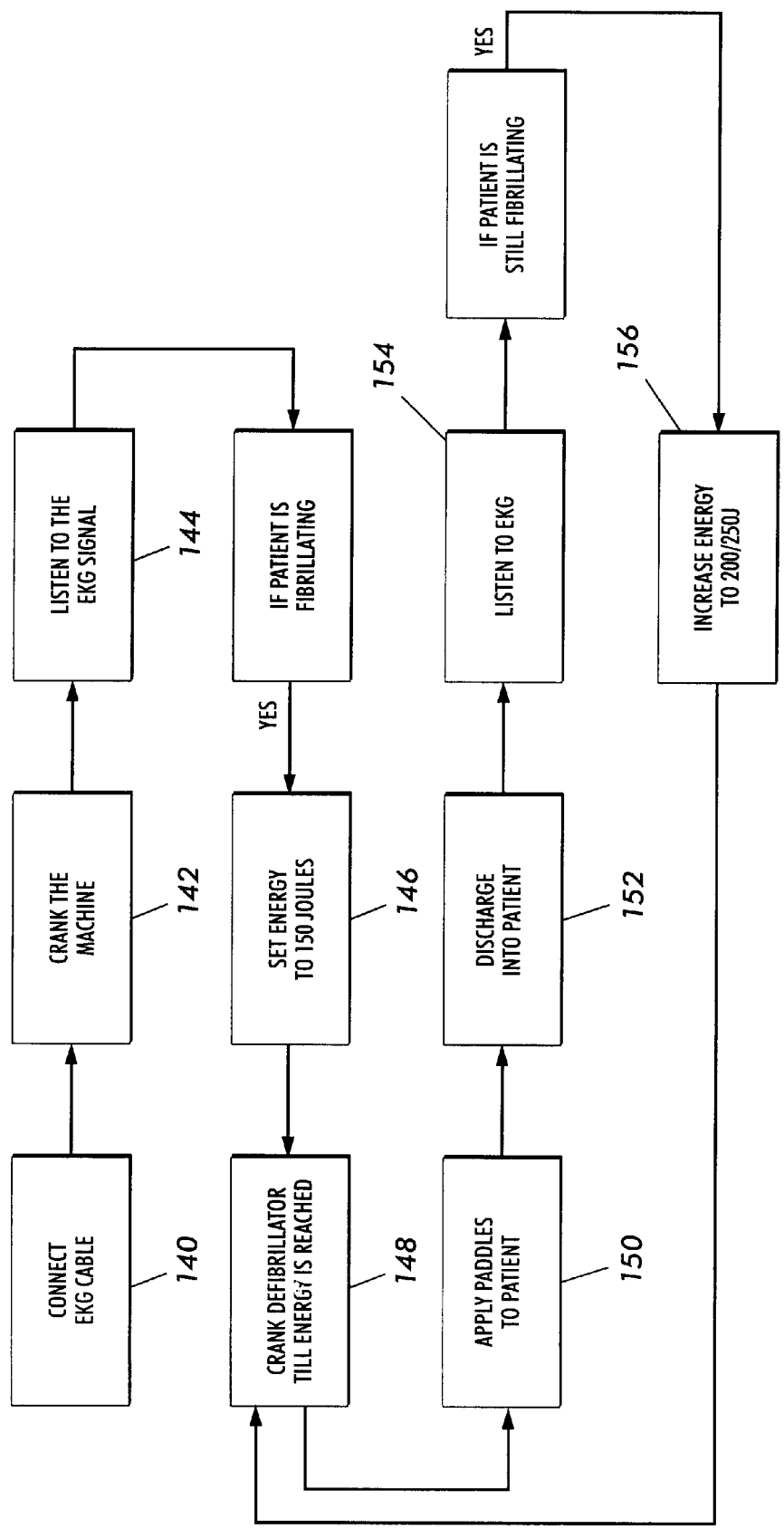
FIG. 8 is a flow diagram illustrating how the defibrillator of this invention preferably is used.

FIG. 8 is a flow diagram illustrating how the defibrillator 10 of FIG. I may be used. In step 140, the EKG cable 18 (see FIG. 1) may be connected via connector 19 to the right arm, the left arm, and the left leg of the patient. Thereafter, in step 142, crank 12 is turned to generate power for device 10. While this is being done, or thereafter, a user may listen to the electrical signals being produced by the patient's heart via headphones 28 in step 144. If such monitoring indicates that the patient is fibrillating, in step 146 an energy level (such as, e.g., 150 Joules) is chosen via control panel 30; and, thereafter, in step 148, crank 12 is turned until the desired energy level is reached, as indicated by the lighting of a light emitting diode corresponding to the desired energy level. Other means can also be used to indicate when the desired energy level has been reached such as, e.g., audio means.

Once the desired energy level has been reached, the paddles 14 and 16 may be applied to the patient in step 150. After the paddles have been applied, in step 152 the desired biphasic pulses are discharged into the patient. One may use on-off switches 21/23 (see FIG. 1) on paddles 14 and 16 to deliver such energy. Concurrently with the delivery of such energy, or thereafter, one may listen to the electrical signals produced by the patient's heart in step 154. If such signals indicate that the patient is still suffering from fibrillation, one may increase the energy level to either 200 and/or 250 Joules in step 156 and repeat one or more of steps 150, 152, and/or 154.

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the following claims.

I claim:

1. An apparatus for defibrillating a human heart that, while alive, provides electrical activity, wherein said apparatus is comprised of mechanical means for producing an alternating voltage, a power factor controller with an input power factor of at least 0.8 for converting said alternating voltage to a first direct voltage, means for converting said first direct voltage into a biphasic waveform voltage, means for sensing said electrical activity of a human heart, and means for transforming said electrical activity of a human heart into an audio signal, wherein:

(a) said biphasic waveform is comprised of a positive pulse and a negative pulse, wherein each of said positive pulse and said negative pulse is a trapezoidal wave, and (b) said mechanical means for producing an alternating voltage is comprised of a multiplicity of generators.

2. The apparatus as recited in claim 1, wherein said mechanical means for producing an alternating voltage is comprised of a crank.

3. The apparatus as recited in claim 2, wherein said crank is operatively connected to at least two dynamos.

4. The apparatus as recited in claim 3, wherein said crank is operatively connected to at least four dynamos.

5. The apparatus as recited in claim 4, wherein said means for sensing the electrical activity of a human heart is comprised of a electrocardiogram cable.

6. The apparatus as recited in claim 5, wherein said electrocardiogram cable is connected to a first electrode, a second electrode, and a third electrode.

7. The apparatus as recited in claim 6, further comprising means for applying said biphasic waveform voltage to said human heart.

8. The apparatus as recited in claim 7, wherein said means for applying said biphasic waveform voltage to a patient is comprised of a first paddle and a second paddle.

9. The apparatus as recited in claim 8, wherein each of said first paddle and said second paddle is comprised of a switch for allowing the flow of electrical energy through said paddle.

10. The apparatus as recited in claim 8, further comprising a headphone connected to said means for transforming the electrical activity of a human heart into an audio signal.

11. The apparatus as recited in claim 8, wherein said positive pulse has a peak voltage which is at least 2 times as great as the peak voltage of said negative pulse.

12. The apparatus as recited in claim 11, wherein each of said positive pulse and said negative pulse has a duration of from about 3 to about 12 milliseconds.

13. The apparatus as recited in claim 12, wherein each of said positive pulse and said negative pulse has a tilt of from about 40 to about 70 percent.

14. The apparatus as recited in claim 9, further comprising means for selecting a desired energy output for said electrical energy flowing through said paddle.

15. The apparatus as recited in claim 10, further comprising a volume control for controlling the volume of the audio signal fed into said headphone.

16. The apparatus as recited in claim 1, wherein said mechanical means for producing an alternating voltage is comprised of from about 4 to about 8 dynamos.

17. The apparatus as recited in claim 16, wherein said power factor controller has an input power factor of at least about 0.99.

18. The apparatus as recited in claim 17, further comprising means for storing electrical energy that is produced by said mechanical means for producing an alternating voltage.

19. The apparatus as recited in claim 18, wherein said means for storing said electrical energy is comprised of a multiplicity of capacitors.

20. The apparatus as recited in claim 1, wherein said means for transforming said electrical activity of a human heart into an audio signal further comprises a modulator.

* * * * *